(12) United States Patent
Veith

(10) Patent No.: US 6,579,984 B1
(45) Date of Patent: Jun. 17, 2003

(54) PROCESS FOR PREPARING 2-AMINO-4-(4-FLUORPHENYL)-6-ALKYLPYRIMIDINE-5-CARBOXYLATE

(75) Inventor: Ulrich Veith, Zurich (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/030,077

(22) PCT Filed: Jun. 30, 2000

(86) PCT No.: PCT/EP00/06099

§ 371 (c)(1),
(2), (4) Date: Mar. 1, 2002

(87) PCT Pub. No.: WO01/04100

PCT Pub. Date: Jan. 18, 2001

Related U.S. Application Data

(60) Provisional application No. 60/185,371, filed on Feb. 28, 2000, and provisional application No. 60/185,465, filed on Feb. 28, 2000.

(30) Foreign Application Priority Data

| Jul. 13, 1999 | (EP) | 99113711 |
| Oct. 14, 1999 | (EP) | 99120417 |
| Mar. 23, 2000 | (EP) | 00106303 |

(51) Int. Cl.[7] .............................. C07D 239/42
(52) U.S. Cl. ..................................... 544/332
(58) Field of Search ................... 544/297, 332

(56) References Cited

U.S. PATENT DOCUMENTS 4,013,706 A  3/1977  Anatol et al. ......... 260/471 C
5,260,440 A  11/1993  Hirai et al. .................. 544/322

FOREIGN PATENT DOCUMENTS

| DE | 3717815  | 12/1988 |
| EP | 0521471  | 1/1993  |
| JP | 6-256318 | 9/1994  |

OTHER PUBLICATIONS

Chem. Berichte, (1958), 91, 759: Korte et al.
Watanabe, M., et al., Bioorg. Med. Chem., (1997), vol. 5, No. 2, 437–444.
Patent Abstracts of Japan, vol. 18, No. 656, (c–1286), Dec. 13, 1994, 06256318A.
Breaux, E.J., et al., J. of Heterocyclic Chemistry, U.S., vol. 18, (Jan. 1981), 183–184.
Kin-Ya, Akiba, et al., J. Am. Chem. Soc., vol. 107, No. 9, (1985), 2721–30.

*Primary Examiner*—John M. Ford
(74) *Attorney, Agent, or Firm*—Fisher, Christen & Sabol

(57) ABSTRACT

A process for the preparation of a compound of the formula:

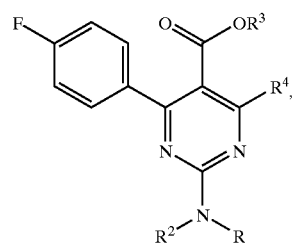

I wherein the variables are herein below defined.

15 Claims, No Drawings

PROCESS FOR PREPARING 2-AMINO-4-(4-FLUORPHENYL)-6-ALKYLPYRIMIDINE-5-CARBOXYLATE

This is 371 of PCT/EP00/06099, filed on Jun. 30, 2000 that has priority benefit of Provisional Application No. 60/185,371, filed on Feb. 28, 2000, and Provisional Application No. 60/185,465, filed on Feb. 28, 2000, and has priority benefit of European Patent Application 00106303.1, filed on Mar. 23, 2000, European Patent Application 99120417.3, filed on Oct. 14, 1999, and European Patent Application 99113711.8, filed on Jul. 13, 1999.

The present invention relates to a novel process for the preparation of compounds of the general formula

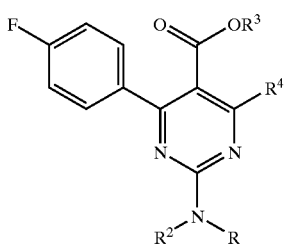

in which R, $R^2$, $R^3$ and $R^4$ have the meaning below.

Compounds of the formula I are important intermediates for the preparation of pharmaceutically active compounds, for example of HMG-Co A reductase inhibitors. Japanese Patent publication JP-A 06 256318, and Watanabe M. et al., *Bioorg. Med. Chem.* 1997, Vol. 5, No. 2, 437–444 describe processes for the preparation of compounds of the formula I.

The process described in JP-A 06 256318 has the disadvantage that three stages are needed in order to prepare 2-amino-4-(4-fluorophenyl)-6-isopropyl-pyrimidine-5-carboxylic acid.

A process for the preparation of ethyl 4-(4-fluorophenyl)-6-isopropyl-2-(N-methanesulphonyl-N-methylamino) pyrimidine-5-carboxylate has been described by Watanabe M. et al., *Bioorg. Med. Chem.* 1997, Vol. 5, No. 2, 437–444. In this process, in the first stage p-fluorobenzaldehyde is converted using ethyl iso-butyrylacetate into an unsaturated ketoester, which is then cyclocondensed in the second stage with S-methylisothiourea hydrogensulphate and subsequently dehydrated in the third stage to give the corresponding pyrimidine. In the fourth stage, this is then oxidized using m-chloroperbenzoic acid to give the corresponding sulphonylpyrimidine, which is then reacted in the fifth stage with methylamine and subsequent treatment with methanesulphonyl chloride to give ethyl 4-(4-fluoro-phenyl)-6-isopropyl-2-(N-methanesulphonyl-N-methyl-amino) pyrimidine-5-carboxylate.

It is disadvantageous in this process, on the one hand, that many reaction stages are necessary and, on the other hand, that the desired product is only formed in moderate yield.

The object of the invention was to make available an economical, industrially feasible process for the preparation of compounds of the formula I.

The object of the invention is achieved by the novel process according to the process of the invention.

According to the invention, compounds of the general formula

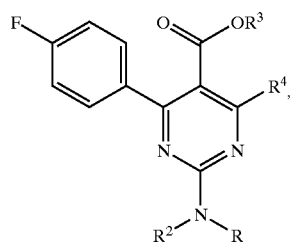

in which
R is hydrogen or a group of the formula —$SO_2R^1$;
$R^1$ is $C_{1-6}$-alkyl;
$R^2$ is hydrogen or $C_{1-6}$-alkyl;
$R^3$ is $C_{1-6}$-alkyl;
$R^4$ is $C_{1-6}$-alkyl,
are prepared in that, in a first stage, a compound of the general formula

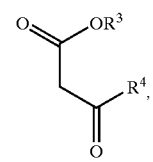

in which $R^3$ and $R^4$ have the abovementioned meaning, is reacted in the presence of a Lewis acid with 4-fluorobenzonitrile to give a compound of the general formula

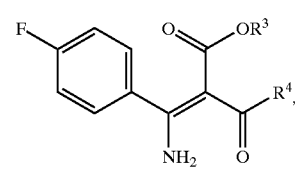

in which $R^3$ and $R^4$ have the abovementioned meaning, and in a second stage the compound of the formula III obtained is reacted with a compound of the general formula

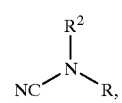

in which R and $R^2$ have the abovementioned meaning, to give the final product of the formula I.

"$C_{1-6}$-alkyl" is understood here and below as meaning linear and branched alkyl groups having 1–6 carbon atoms, such as, for example, methyl, ethyl, propyl, isopropyl, butyl, tert-butyl, isobutyl, sec-butyl, pentyl and its isomers and hexyl and its isomers.

The compounds of the formula II can be prepared according to *Chem. Berichte* 1958, 91, 759 or are commercially available organic synthetic chemicals.

4-Fluorobenzonitrile is a commercially available organic synthetic chemical.

The Lewis acid employed in the first stage is expediently an aprotic Lewis acid such as, for example, tin tetrachloride, titanium tetrachloride or aluminium chloride. Tin tetrachloride is preferably employed.

The first stage is expediently carried out in the presence of an organic solvent. The organic solvents employed can be, for example, aromatic hydrocarbons, chlorinated aromatic and aliphatic hydrocarbons. Aromatic hydrocarbons employed are preferably toluene, benzene or xylene. The chlorinated aromatic hydrocarbon employed is preferably chlorobenzene; the chlorinated aliphatic hydrocarbon employed is preferably 1,2-dichloroethane. Toluene and 1,2-dichloroethane are particularly preferably employed.

The reaction in the first stage is expediently carried out at a temperature from −5 to 140° C., advantageously at 60 to 100° C.

After a reaction time of 30 min to 6 h and subsequent hydrolysis, the compounds of the formula III can be isolated by known methods such as, for example, by extraction or can be employed directly, without isolation, for the second stage. The intermediate (formula III) is preferably isolated.

Compounds of the formula III include cis and trans isomers.

In a second stage, a compound of the formula III is reacted with a compound of the formula IV to give the final product of the formula I.

The invention comprises, on the one hand, compounds of the formula I in which R and $R^2$ are hydrogen. These compounds are prepared by reaction of compounds of the formula III with cyanamide.

The reaction with cyanamide is expediently carried out in the presence of an organic solvent, a mixture of water with an organic solvent or in water. Water is particularly preferably employed. Organic solvents employed are advantageously toluene or ethyl acetate. Organic solvents employed as a mixture with water are advantageously alcohols such as, for example, methanol, ethers such as, for example, dioxane or aromatic hydrocarbons such as, for example, toluene or N,N-dimethylacetamide.

The reaction with cyanamide is expediently carried out at a temperature of 10 to 120° C., advantageously at 40 to 100° C. The pH is expediently in a range from 3 to 9, advantageously in a range from 4 to 7. After a reaction time of, in total, 1 to 20 h, the compounds of the general formula I are obtained, which can be worked up according to known methods.

In a particular embodiment, 2-amino-4-(4-fluorophenyl)-6-isopropylpyrimidine-5-carboxylic acid esters of the general formula

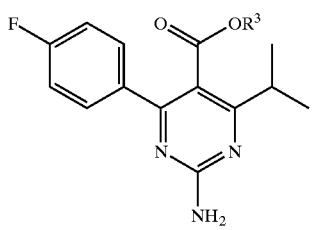

Ia in which $R^3$ has the meaning indicated in formula I are prepared in that, in a first stage, an alkyl iso-butyrylacetate of the general formula

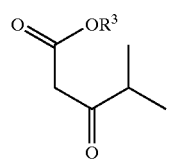

IIa in which $R^3$ has the meaning mentioned is reacted in the presence of a Lewis acid with 4-fluorobenzonitrile to give a 2-[1-amino-1-(4-fluorophenyl)methylene]-4-methyl-3-oxopentanoic acid ester of the general formula

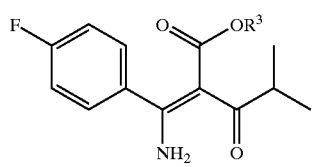

IIIa and in a second stage the compound of the formula IIIa is reacted with cyanamide of the formula

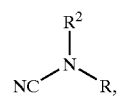

IVa in which R and $R^2$ are hydrogen, to give the final product of the formula Ia.

The radical $R^3$ is preferably methyl.

The compounds of the formula III are novel and also a subject of the invention.

The invention comprises, on the other hand, compounds of the formula I in which R is a group of the formula $-SO_2R^1$ and $R^1$ and $R^2$ are $C_{1-6}$-alkyl. These 4-(4-fluorophenyl)-6-alkyl-2-(N-alkanesulphonyl-N-alkylamino)pyrimidine-5-carboxylic acid esters of the general formula

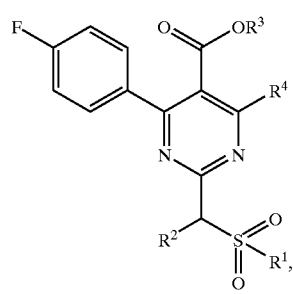

Ib in which $R^1$, $R^2$, $R^3$ and $R^4$ are identical or different and are a $C_{1-6}$-alkyl group, can be prepared in that 2-[1-amino-1-(4-fluorophenyl)methylene]-4-alkyl-3-oxo-alkanoic acid esters of the general formula

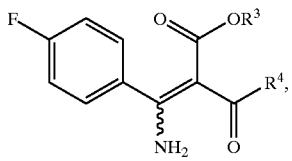

IIIb in which $R^3$ and $R^4$ have the abovementioned meaning, are reacted with N-cyano-N-alkylalkanesulphonamides, optionally isolated or prepared in situ, of the general formula

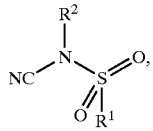

IVb in which $R^1$ and $R^2$ are a $C_{1-6}$-alkyl group.

The reaction can be carried out either in the presence of a base or in the presence of a Lewis acid.

Bases which can be employed are alkali metal compounds such as, for example, alkali metal hydrides, alkali metal carbonates, alkali metal alkoxides or alkali metal silazanes. Alkali metal carbonates which can be used are lithium, sodium or potassium carbonate. The alkali metal hydride employed can be potassium, lithium or sodium hydride; sodium hydride is preferably employed. The alkali metal alkoxide employed can be sodium or potassium tert-pentoxide or sodium or potassium tert-butoxide, preferably sodium tert-pentoxide or sodium tert-butoxide. The alkali metal silazane used can be sodium hexamethyldisilazane or potassium hexamethyldisilazane. The base preferably employed is an alkali metal hydride or an alkali metal alkoxide.

The reaction is expediently carried out in the presence of a base in a polar organic solvent. The polar solvent used can be, for example, N,N-dimethyl-acetamide, isopropanol, tert-butanol, toluene, di-methylformamide, tetrahydrofuran, 1,4-dioxane or mixtures of these. N-Alkylalkanesulphonamides such as, for example, N-methylmethanesulphonamide are likewise suitable as solvents. The reaction is preferably carried out in N-alkylalkanesulphonamide and tert-butanol.

The reaction can be carried out in the presence of a base at a temperature from –10 to 150° C., preferably from 0 to 80° C.

The reaction of compounds of the formula IIIb with compounds of the formula IVb in the presence of a Lewis acid is expediently carried out in the solvent which is inert to the Lewis acid. Inert solvents which can be employed are, for example, aromatic hydrocarbons, and chlorinated aromatic and aliphatic hydrocarbons. Aromatic hydrocarbons employed are preferably toluene or xylene. The chlorinated aromatic hydrocarbon employed is preferably chlorobenzene; chlorinated aliphatic hydrocarbons employed are preferably dichloromethane or 1,2-dichloroethane.

The reaction in the presence of a Lewis acid can be carried out at a temperature from 20 to 150° C., preferably from 80 to 120° C.

Suitable Lewis acids are for example $TiCl_4$, $TiBr_4$ or $SnCl_4$. Titanium tetrachloride is preferred.

The amount of Lewis acid is 0.1 to 2 molar equivalents based on the compound of the formula IIIb.

After a reaction time of 1 to 24 h, the final products of the general formula Ib can be isolated by known working-up methods.

In a preferred embodiment, the final product of the formula Ib isolated is ethyl 4-(4-fluorophenyl)-6-isopropyl-2-(N-methanesulphonyl-N-methylamino)-pyrimidine-5-carboxylate ($R^1=R^2=R^3$=methyl, $R^4$=isopropyl).

Compounds of the formula IVb are expediently prepared in that a compound of the general formula

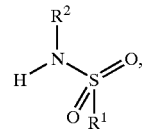

V in which $R^1$ and $R^2$ are $C_{1-6}$-alkyl, is reacted with cyanogen halide in the presence of a base.

Suitable bases are the bases described beforehand.

The cyanogen halide employed can be cyanogen fluoride, cyanogen chloride, cyanogen bromide or cyanogen iodide. Cyanogen chloride or cyanogen bromide is preferably employed.

This reaction can likewise be carried out in the polar organic solvents described beforehand. The reaction is preferably carried out in tetrahydrofuran.

The reaction is expediently carried out at a temperature from –20 to 50° C., preferably at a temperature from –10 to +20° C.

After a reaction time of ¾ to 1 h, the compounds of the formula IVb, which have not yet been described in the literature, can then be isolated in a manner known to the person skilled in the art.

These compounds of the formula IVb are also a subject of the invention.

Compounds of the formula IVb can be prepared in situ, i.e. they are formed directly from the corresponding starting materials during the reaction without isolation. However, they can also be prepared and isolated separately in order then to employ them for the reaction.

Examples of compounds of the formula IVb are: N-cyano-N-methylmethanesulphonamide, N-cyano-N-ethyl-methanesulphonamide, N-cyano-N-propylmethanesulphonamide, N-cyano-N-butylmethanesulphonamide, N-cyano-N-pentylmethanesulphonamide and N-cyano-N-hexylmethanesulphonamide. N-Cyano-N-methylmethanesulphonamide is preferred.

The compounds of the formula I can also be prepared in that a compound of the general formula

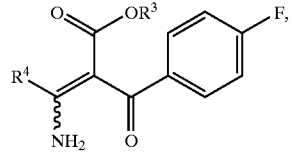

VI in which $R^3$ and $R^4$ have the meaning mentioned in claim 1, is reacted with a compound of the formula IV.

The reaction is carried out analogously to the reaction of the compounds of the formula III with compounds of the formula IV, preferably in the presence of a base in a polar organic solvent at a temperature from –10 to 150° C.

Suitable bases and solvents correspond to the bases and solvents which are listed under the reaction of compounds of the formula III with compounds of the formula IV.

In a preferred embodiment, compounds of the general formula Ib are prepared in that a compound of the formula VI is reacted with a compound of the formula IVb in a polar organic solvent at a temperature from 0 to 80° C. in the presence of a base.

The compounds of the formula VI can be prepared by reaction of $C_{1-6}$-alkyl nitriles with $C_{1-6}$-alkyl 4-fluorobenzoylacetate in the presence of a Lewis acid. A compound of the formula VI in which $R^3$ is methyl and $R^4$ is isopropyl is preferred. The Lewis acid is preferably tin tetrachloride. The reaction is expediently carried out in a polar solvent. Suitable solvents correspond to the solvents which are listed under the reaction of compounds of the formula II with compounds of the formula III described above. The reaction in the first stage is expediently carried out at a temperature from −5 to 140° C., advantageously at 60 to 100° C.

The compounds of the formula VI are novel and likewise a subject of the invention.

EXAMPLES

Example 1

Methyl 2-[1-amino-1-(4-fluorophenyl)methylene]-4-methyl-3-oxopentanoate

IIIa, $R^3$=Methyl, Toluene, $SnCl_4$ 1.50 g of methyl isobutyrylacetate (10.0 mmol, concentration 96%) and 1.24 g of 4-fluorobenzonitrile (10 mmol, concentration 98%) were dissolved in 10 ml of toluene and treated with 2.63 g of tin tetrachloride (10 mmol, concentration 99%) at room temperature over the course of 6 min. After 3 h at room temperature, the mixture was heated to 80° C. After 2.5 h, the suspension was again cooled to room temperature and treated with 10 ml of water. It was diluted with 5 ml of ethyl acetate and the phases were separated. After extraction of the aqueous phase with ethyl acetate (2×5 ml), the combined organic phases were dried over magnesium sulphate. After concentration in vacuo, 3.50 g of crude product were obtained in the form of a pale yellow, tacky solid. The solid was dissolved in ethyl acetate and purified by flash chromatography (n-hexane/ethyl acetate 5:1 to 1:1). After concentration in vacuo, 1.44 g of methyl 2-[1-amino-1-(4-fluorophenyl)-methylene]-4-methyl-3-oxopentanoate were obtained.

Yield: 54.3% (concentration >99%) in the form of a colourless solid.

Melting point: 85.8–86.6° C.

Example 2

Methyl 2-[1-amino-1-(4-fluorophenyl)methylene]-4-methyl-3-oxopentanoate

IIIa, $R^3$=Methyl, Toluene, $SnCl_4$ 22.53 g of methyl isobutyrylacetate (0.15 mol, concentration 96%) and 18.54 g of 4-fluorobenzonitrile (0.15 mol, concentration 98%) were dissolved in 150 ml of toluene and treated with 43.32 g of tin tetrachloride (0.165 mol, concentration 99%) at room temperature over the course of 12 min. After half an hour at room temperature, the mixture was heated to 80° C. After 3 h, the suspension was cooled to room temperature and treated with 150 ml of water. It was diluted with 100 ml of ethyl acetate and the phases were separated. After extraction of the aqueous phase with ethyl acetate (2×100 ml), the combined organic phases were washed with 100 ml of saturated aqueous sodium hydrogencarbonate solution and 100 ml of 1N sodium hydroxide solution and dried over magnesium sulphate. After concentration in vacuo, 46.46 g of crude product were obtained in the form of a yellowish solid. The solid was dissolved in a mixture of 50 ml of n-hexane and 5 ml of toluene under reflux and filtered hot. The product precipitated from the filtrate on cooling. By filtering through a frit and washing the filter cake with 2×40 ml of n-hexane, 32.42 g of methyl 2-[1-amino-1-(4-fluorophenyl)methylene]-4-methyl-3-oxopentanoate were obtained in the form of a spectroscopically pure solid.

Yield: 80.7% (concentration 99.0%)

Melting point: 84.0–84.9° C.

$^1$H NMR (DMSO-$d^6$, 400 MHz): δ=0.98 (d, 6H); 3.06 (sept, 1H); 3.24 (s, 3H); 7.27 (t, 2H); 7.35 (m, 2H); 8.38 (s, 1H); 10.59 (s, 1H).

$^{13}$C NMR (DMSO-$d^6$, 100 MHz): δ=19.45 (q); 36.04 (d); 50.74 (q); 101.54 (s); 115.11 (sd); 115.33 (sd); 129.16 (dd); 129.25 (dd); 133.68 (sd); 161.46.54 (s); 163.91 (s); 165.59 (s); 169.71 (s); 201.10 (s).

Example 3

Methyl 2-[1-amino-1-(4-fluorophenyl)methylene]-4-methyl-3-oxopentanoate

IIIa, $R^3$=Methyl, Toluene, $SnCl_4$ 75.09 g of methyl isobutyrylacetate (0.50 mol, concentration 96%) and 61.80 g of 4-fluorobenzonitrile (0.50 mol, concentration 98%) were introduced into [500 ml of toluene and treated with 144.7 g of tin tetrachloride (0.55 mol, concentration 99%) at room temperature over the course of 16 min. After half an hour at room temperature, the thick suspension was heated to 80° C. After 3 h, 175 ml of toluene were distilled off at normal pressure, and the mixture was cooled to room temperature and treated with 450 ml of saturated sodium carbonate and 300 ml of ethyl acetate. The organic phase was separated off and the aqueous phase (after dilution with 300 ml of water) was again extracted with 300 ml of ethyl acetate. After drying the combined organic phases over sodium sulphate, the solvent was removed in vacuo (40° C./25 mbar). 127.2 g of crude product were obtained in the form of a slightly yellowish solid, which was dissolved in 160 ml of n-hexane (slightly turbid solution). After hot filtration and subsequent cooling in an ice bath, 99.8 g of methyl 2-[1-amino-1-(4-fluorophenyl)-methylene]-4-methyl-3-oxopentanoate were obtained after filtration in the form of a pale yellow solid.

Yield: 74.5% (concentration 99.3%)

Melting point: 86.4–87.8° C.

Example 4

Methyl 2-[1-amino-1-(4-fluorophenyl)methylene]-4-methyl-3-oxopentanoate

IIIa, $R^3$=Methyl, 1,2-dichloroethane, $AlCl_3$ 754 mg of methyl isobutyrylacetate (5.00 mmol, concentration 96%) and 618 mg of 4-fluorobenzonitrile (5.00 mmol, concentration 98%) were introduced into 5 ml of 1,2-dichloroethane and treated with 673 mg of aluminium chloride (5.00 mol) at room temperature. After one hour at room temperature, the mixture was heated to 80° C. After 19 h—the mixture contained 13.9 area per cent of product according to HPLC analysis—the mixture was cooled to room temperature and treated with water (5 ml). The organic phase was separated off and the aqueous phase was extracted with dichloromethane (3×5 ml). The combined organic phases were dried over magnesium sulphate and concentrated in vacuo. 1.01 g of crude product were obtained, which contained 3% (30 mg) of methyl 2-[1-amino-1-(4-fluorophenyl)methylene]-4-methyl-3-oxopentanoate according to $^1$H-NMR spectrum.

Example 5

Methyl 2-[1-amino-1-(4-fluorophenyl)methylene]-4-methyl-3-oxopentanoate

IIIa, $R^3$=Methyl, Toluene, $SnCl_4$ 75.09 g of methyl isobutyrylacetate (0.50 mol, concentration 96%) and 61.8 g of 4-fluorobenzonitrile (0.50 mol, concentration 98%) were dissolved in 500 ml of toluene and treated with 144.72 g of tin tetrachloride (0.55 mol, concentration 99%) at room temperature over the course of 15 min. After half an hour at room temperature, the mixture was heated to 80° C. After 3 h, the suspension was cooled to 10° C. and treated with 500 ml of water. The mixture was diluted with 100 ml of dichloroethane and the phases were separated. The organic phase was washed with 2×100 ml of 1N sodium hydroxide solution. After concentration in vacuo, 125.5 g of crude product were obtained in the form of a yellowish solid. The solid was dissolved in 160 ml of n-hexane under reflux and filtered hot. The product precipitated from the filtrate on cooling. By filtering through a frit and washing the filter cake with 130 ml of n-hexane, 79.8 g of methyl 2-[1-amino-1-(4-fluorophenyl)methylene]-4-methyl-3-oxopentanoate were obtained in the form of a spectroscopically pure solid.

Yield: 60.7% (concentration 98.7%)

Melting point: 88.4–89.3° C.

Example 6

Methyl 2-amino-4-(4-fluorophenyl)-6-isopropylpyrimidine-5-carboxylate

Ia, $R^3$=Methyl, Water

A suspension of 1.33 g of methyl 2-[1-amino-1-(4-fluorophenyl)methylene]-4-methyl-3-oxopentanoate (5.00 mmol) in 4.20 g of 50% strength aqueous cyanamide solution (50.0 mmol) was heated to reflux. After 17 h, it was cooled to room temperature and treated with ethyl acetate (5 ml) and water (5 ml). The undissolved solid was filtered off. The organic phase was separated off and the aqueous phase was extracted with ethyl acetate (2×5 ml). The combined organic phases were dried over magnesium sulphate and concentrated in vacuo. The crude product (0.97 g) was purified by flash chromatography on silica gel (eluent: methylene chloride). 121.6 mg of methyl 2-amino-4-(4-fluorophenyl)-6-isopropylpyrimidine-5-carboxylate were obtained in the form of a colourless solid.

Yield: 8.4%

Melting point: 146.2–147.0° C.

$^1$H NMR (DMSO-$d^6_1$, 400 MHz): δ=1.08 (d, 6H); 3.04 (sept, 1H); 3.57 (s, 3H); 7.05 (s, broad, 2H); 7.28 (m, 2H); 7.53 (m, 2H).

Example 7

Methyl 2-amino-4-(4-fluorophenyl)-6-isopropylpyrimidine-5-carboxylate

Ia, $R^3$=Methyl, N,N-dimethylacetamide 5.00 g of methyl 2-[1-amino-1-(4-fluorophenyl)-methylene]-4-methyl-3-oxopentanoate (18.7 mmol) were treated with 5 ml of N-N-dimethylacetamide and 15.71 g of a 50% strength aqueous cyanamide solution (187 mmol) and heated to reflux. After 5 h, the solution was poured onto 50 ml of water. The mixture was cooled in an ice bath and the deposited precipitate was isolated by means of a suction filter. After drying, 2.72 g of crude product were obtained in the form of a yellowish solid. After flash chromatography (150 g of silica gel; eluent: hexane/ethyl acetate 3:2), 1.19 g of methyl 2-amino-4-(4-fluorophenyl)-6-isopropylpyrimidine-5-carboxylate were isolated in the form of a colourless solid.

Yield: 22.0%

Melting point: 145–146° C.

Example 8

N-Cyano-N-methylmethanesulphonamide

IVb, $R^1$=$R^2$=Methyl 12.22 g (0.28 mol) of sodium hydride (55% in oil) were twice suspended in 100 ml of n-hexane under nitrogen and freed from the oil by means of a frit. The hexane-moist sodium hydride was taken up in 200 ml of tetrahydrofuran and cautiously treated at 2° C. with 22.98 g (0.20 mol) of N-methylmethanesulphonamide (concentration 95%). Evolution of gas was observed. After addition was complete (25 min), the cooling bath was removed and the mixture was subsequently reacted at room temperature for 3 h 40 min until evolution of hydrogen was no longer observed. The mixture was subsequently cooled again using an ice bath and 20.0 g (0.32 mol) of cyanogen chloride (concentration 99%) were cautiously introduced over the course of 40 min (slightly exothermic). After subsequent reaction at 0–5° C. for 45 min, the reaction mixture was poured onto 200 ml of ice water. The phases were separated and the aqueous phase was extracted with 1×200 ml and two times 100 ml of diethyl ether. The organic phases were combined and dried over magnesium sulphate. After filtration and concentration in vacuo, 26.57 g of crude product were obtained in the form of a yellowish, two-phase oil, which partially crystallized in the refrigerator. After distillation in vacuo (boiling point 90–95° C./0.01 mbar), 17.24 g of N-cyano-N-methylmethanesulphonamide were obtained in the form of a colourless oil, which crystallized in the refrigerator.

Yield: 61.7%, [concentration: 96.0% (GC)]

Melting point: 29–30° C.

Example 9

N-Cyano-N-methylmethanesulphonamide

IVb, $R^1$=$R^2$=Methyl 36.65 g (0.84 mol) of sodium hydride (55% in oil) were suspended three times in 200 ml of n-hexane under nitrogen and freed from the oil by means of a frit. The hexane-moist sodium hydride was taken up in 600 ml of tetrahydrofuran and cautiously treated at 2° C. with 68.94 g (0.60 mol) of N-methylmethanesulphonamide (concentration 95%). Evolution of gas was observed. After addition was complete (45 min), the cooling bath was removed and the mixture was subsequently reacted at room temperature for 4 h 25 min until evolution of hydrogen was no longer observed. It was subsequently cooled again using an ice bath and 59.6 g (0.96 mol) of cyanogen chloride (concentration 99%) were cautiously introduced over the course of 1 h 45 min (slightly exothermic). After subsequent reaction at 0–5° C. for 20 min, the reaction mixture was poured onto 600 ml of ice water. The phases were separated and the aqueous phase was extracted with 2×500 ml of diethyl ether. The combined organic phases were dried over magnesium sulphate. After filtration and concentration in vacuo, 99.22 g of crude product were obtained, which crystallized at 15° C. After filtration, 70.56 g of crude product were isolated in the form of a tacky, colourless solid. After distillation in vacuo (boiling point 90–95° C./0.01 mbar), 57.4 g of N-cyano-N-methyl-methanesulphonamide were obtained in the form of a colourless oil, which crystallized in the refrigerator.

Yield: 71.3%, [concentration: >99% (GC)]
Melting point: 29.0–30.0° C.
$^1$H NMR (DMSO-d$^6$, 400 MHz): δ=3.28 (s, 3H); 3.48 (s, 3H).
$^{13}$C NMR (DMSO-d$^6$, 100 MHz): δ=35.46 (q); 37.74 (q); 109.35 (s).

Example 10

N-Cyano-N-methylmethanesulphonamide

IVb, R$^1$=R$^2$=Methyl 36.7 g (0.84 mol) of sodium hydride (55% in oil) were suspended three times in 200 ml of n-hexane under nitrogen and freed from the oil by means of a frit. The hexane-moist sodium hydride was taken up in 600 ml of tetrahydrofuran and cautiously treated at 2° C. with 68.94 g (0.60 mol) of N-methylmethanesulphonamide (concentration 95%). Evolution of gas was observed. After addition was complete (30 min), the cooling bath was removed and the mixture was subsequently reacted at room temperature for 4 h until evolution of hydrogen was no longer observed. It was subsequently cooled again using an ice bath and 59.6 g (0.96 mol) of cyanogen chloride (concentration 99%) were cautiously introduced over the course of 2 h (slightly exothermic). After subsequent reaction at 0–5° C. for 20 min, the reaction mixture was poured onto 600 ml of ice water. After addition of 500 ml of diethyl ether, the phases were separated and the aqueous phase was extracted with 500 ml of diethyl ether. The combined organic phases were dried over magnesium sulphate. After filtration and concentration in vacuo, 99.22 g of crude product were obtained, which crystallized at 15° C. After filtration, 86.5 g of crude product were isolated in the form of a tacky, colourless solid. After distillation in vacuo (boiling point 91–93° C./0.1 mbar), 72.9 g of N-cyano-N-methylmethanesulphonamide were obtained in the form of a colourless oil which crystallized in the refrigerator.

Yield: 90.6%, [concentration: >99% (GC)]

Example 11

Methyl 4-(4-fluorophenyl)-6-isopropyl-2-(N-methanesulphonyl-N-methylamino)pyrimidine-5-carboxylate Ib, R$^1$=R$^2$=R$^3$=Methyl, R$^4$=Isopropyl, NaH 2.66 g (10.0 mmol) of methyl 2-[1-amino-1-(4-fluorophenyl)methylene]-4-methyl-3-oxopentanoate were introduced into 12 g of N,N-dimethylacetamide together with 2.70 g (20.0 mmol) of N-cyano-N-methylmethanesulphonamide. 440 mg (11.0 mmol) of sodium hydride (60% in oil) were added to this solution at room temperature over the course of 2 h. An orange-red clear solution was obtained. After 6 h at room temperature, the reaction solution was poured onto 25 ml of water. The suspension was stirred in an ice bath for 30 minutes, and the precipitate was filtered off and washed with water (2×10 ml). After drying in a high vacuum, 1.11 g (29.1%) of methyl 4-(4-fluorophenyl)-6-isopropyl-2-(N-methanesulphonyl-N-methylamino)pyrimidine-5-carboxylate were obtained in the form of a pale beige solid. The product still contained traces of methyl 2-[1-amino-1-(4-fluorophenyl)methylene]-4-methyl-3-oxopentanoate.

$^1$H NMR (DMSO-d$^6$, 400 MHz): δ=1.15 (d, 6H); 3.17 (sept, 1H); 3.50 (s, 3H); 3.58 (s, 3H); 3.73 (s, 3H); 7.39 (m, 2H); 7.69 (m, 2H).

Example 12

Methyl 4-(4-fluorophenyl)-6-isopropyl-2-(N-methanesulphonyl-N-methylamino)pyrimidine-5-carboxylate Ib, R$^1$=R$^2$=R$^3$=Methyl, R$^4$=Isopropyl, Sodium Tert-pentoxide 2.66 g (10.0 mmol) of methyl 2-[1-amino-1-(4-fluorophenyl)methylene]-4-methyl-3-oxopentanoate were introduced into 7 g of N,N-dimethylacetamide together with 2.70 g (20.0 mmol) of N-cyano-N-methylmethanesulphonamide. 1.21 g (11.0 mmol) of sodium tert-pentoxide in 5 g of dimethylacetamide were added to this solution at room temperature after the course of 3 h. An orange-red clear solution was obtained. After 2.5 h at room temperature, the reaction solution was poured onto 25 ml of water. The suspension was stirred in an ice bath for 30 minutes, and the precipitate was filtered off and washed with water (10 ml). After drying in a high vacuum, 1.65 g of crude product were obtained in the form of a pale beige solid which contained 676.5 mg of methyl 4-(4-fluorophenyl)-6-isopropyl-2-(N-methanesulphonyl-N-methylamino)-pyrimidine-5-carboxylate.

Yield: 17.7%

Example 13

Methyl 4-(4-fluorophenyl)-6-isopropyl-2-(N-methanesulphonyl-N-methylamino)pyrimidine-5-carboxylate Ib, R$^1$=R$^2$=R$^3$=Methyl, R$^4$=Isopropyl, NaH 10.0 g (37.7 mmol) of methyl 2-[1-amino-1-(4-fluorophenyl)methylene]-4-methyl-3-oxopentanoate were introduced into 45 ml of N,N-dimethylacetamide together with 15.2 g (113 mmol) of N-cyano-N-methylmethanesulphonamide. 3.50 g (88.7 mmol) of sodium hydride (60% in oil) were added at room temperature to this solution. An orange-red viscous solution was obtained. The reaction solution was poured onto 120 ml of water and stirred in an ice bath for 30 minutes. The precipitate was filtered off and washed with water (10 ml). After drying in a high vacuum, 4.60 g of crude product were obtained in the form of a pale beige solid. According to the $^1$H NMR spectrum, the solid contained an 84:16 product/starting material mixture, which corresponds to a yield of 27% of methyl 4-(4-fluorophenyl)-6-isopropyl-2-(N-methanesulphonyl-N-methylamino)pyrimidine-5-carboxylate.

Example 14

Methyl 4-(4-fluorophenyl)-6-isopropyl-2-(N-methanesulphonyl-N-methylamino)pyrimidine-5-carboxylate Ib, R$^1$=R$^2$=R$^3$=Methyl, R$^4$=Isopropyl, NaH, Compound of the Formula IVb Formed in situ 2.65 g (10.0 mmol) of methyl 2-[1-amino-1-(4-fluorophenyl)methylene]-4-methyl-3-oxopentanoate were introduced into 5 g of N-N-dimethylacetamide together with 2.30 g (20.0 mmol) of N-methylmethanesulphonamide. 470 mg (20.0 mmol) of sodium hydride (60% in oil) were added to this solution at room temperature. The reaction solution was treated with 2.40 g (40.0 mmol) of cyanogen chloride at room temperature. After 20 h, the mixture was poured onto 40 ml of water and the yellowish suspension was cooled in an ice bath. The precipitate deposited was filtered off and washed with 20 ml of water. After drying in vacuo, 2.22 g of crude product were obtained in the form of a pale beige solid, which according to the $^1$H NMR spectrum contained a 70:30 starting material/product mixture, which corresponds to a yield of 22% of methyl 4-(4-fluorophenyl)-6-isopropyl-2-(N-methanesulphonyl-N-methylamino)pyrimidine-5-carboxylate.

Example 15

Methyl 4-(4-fluorophenyl)-6-isopropyl-2-(N-methanesulphonyl-N-methylamino)pyrimidine-5-carboxylate Ib, $R^1=R^2=R^3$=Methyl, $R^4$=Isopropyl, NaH, Compound of the Formula IVb Formed in situ 13.3 g (50.0 mmol) of methyl 2-[1-amino-1-(4-fluorophenyl)methylene]-4-methyl-3-oxopentanoate were introduced into 25 g of N,N-dimethylacetamide together with 10.9 g (100.0 mmol) of N-methylmethanesulphonamide. 3.60 g (90.0 mmol) of sodium hydride (60% in oil) were added to this solution at 25° C. Vigorous foaming was observed. After 15 min at 25° C., 6.0 g (100.0 mmol) of cyanogen chloride gas were introduced after the course of 20 min. An orange-coloured suspension was formed. This was stirred at 25° C. for 2 h and 2.40 g (60.0 mmol) of sodium hydride (60% in oil) and subsequently 6.0 g (100.0 mmol) of cyanogen chloride were added again. The mixture was stirred at 25° C. again for 1 h before a further 3.60 g (90.0 mmol) of sodium hydride (60% in oil) were added. The reaction mixture was poured onto an ice/water mixture (200 ml) and stirred at 0° C. for 1 h. The resulting solid was filtered off and washed with 100 ml of water. After drying in a high vacuum, 14.62 g of crude product were obtained in the form of a beige solid. 8.22 g of this solid were recrystallized in an acetone/water mixture. 4.24 g of product were obtained in the form of a pale beige solid, which corresponds to a yield of 29% [concentration (GC) 72%].

Example 16

Methyl 4-(4-fluorophenyl)-6-isopropyl-2-(N-methanesulphonyl-N-methylamino)pyrimidine-5-carboxylate Ib, $R^1=R^2=R^3$=Methyl, $R^4$=Isopropyl, NaH, Compound of the Formula IVb Formed in situ 13.3 g (50.0 mmol) of methyl 2-[1-amino-1-(4-fluorophenyl)methylene]-4-methyl-3-oxopentanoate were introduced into 25 g of N,N-dimethylacetamide together with 10.9 g (100.0 mmol) of N-methylmethanesulphonamide. 3.60 g (90.0 mmol) of sodium hydride (60% in oil) were added to this solution at 25° C. Vigorous foaming was observed. After 25 min at 25° C., 6.0 g (100.0 mmol) of cyanogen chloride gas were introduced after the course of 12 min. During this, the temperature rose temporarily to 32° C. An orange-coloured suspension was formed. The mixture was stirred at 25° C. for 1 h 25 min and 2.40 g (60.0 mmol) of sodium hydride (60% in oil) and subsequently 3.0 g (50.0 mmol) of cyanogen chloride were added again. The mixture was stirred at 25° C. again for 1 h 40 min before a further 2.40 g (60.0 mmol) of sodium hydride (60% in oil) and 3.0 g (50.0 mmol) of cyanogen chloride were added. After addition of a further 2.40 g (60.0 mmol) of sodium hydride (60% in oil), the reaction mixture was poured onto an ice/water mixture (200 ml). The apparatus was washed with 50 ml of water and tie mixture was stirred at 0° C. for 1 h. The resulting solid was filtered off and washed with 50 ml of water. After drying in a high vacuum, 10.47 g of crude product were obtained in the form of a beige solid. 8.00 g of this solid were recrystallized in an acetone/water mixture. 5.50 g of product were obtained in the form of a pale beige solid, which corresponded to a yield of 30.2% [concentration (GC) 80%].

Example 17

Methyl 4-(4-fluorophenyl)-6-isopropyl-2-(N-methanesulphonyl-N-methylamino)pyrimidine-5-carboxylate Ib, $R^1=R^2=R^3$=Methyl, $R^4$=Isopropyl, NaH, Compound of the Formula IVb Formed in situ 13.3 g (50.0 mmol) of methyl 2-[1-amino-1-(4-fluorophenyl)methylene]-4-methyl-3-oxopentanoate were introduced into 50.0 g (0.46 mol) of N-methylmethanesulphonamide. 12.0 g (0.30 mol) of sodium hydride (60% in oil) were added to this solution at 25° C. after the course of 1 h 45 min. Vigorous foaming was observed. In order to guarantee better stirrability, 30.0 g (0.275 mol) of N-methyl-methane-sulphonamide were added again during the addition. After 30 min at 25° C., 15.0 g (0.25 mol) of cyanogen chloride gas were introduced over the course of 50 min. The suspension was transferred to an autoclave and stirred at 60° C. for 18.5 h. The reaction mixture was poured onto an ice/water mixture (200 ml) and stirred at 0° C. for 30 min. The resulting solid was filtered off and washed with 50 ml of water. After drying in a high vacuum, 18.71 g of crude product were obtained in the form of a beige solid. 10.0 g of this solid were recrystallized in an acetone/water mixture. 5.40 g of methyl 4-(4-fluorophenyl)-6-isopropyl-2-(N-methanesulphonyl-N-methylamino)pyrimidine-5-carboxylate were obtained in the form of a colourless solid.

Yield of 50.6%, [concentration 95.5% (GC)].

Example 18

Methyl 4-(4-fluorophenyl)-6-isopropyl-2-(N-methanesulphonyl-N-methylamino)pyrimidine-5-carboxylate Ib, $R^1=R^2=R^3$=Methyl, $R^4$=Isopropyl, Sodium Tert-pentoxide, Compound of the Formula IVb Formed in situ 13.3 g (50.0 mmol) of methyl 2-[1-amino-1-(4-fluorophenyl)methylene]-4-methyl-3-oxopentanoate were introduced into 50.0 g (0:46 mol) of N-methylmethanesulphonamide. 33.0 g (0.30 mol) of sodium tert-pentoxide were added to this solution at 25° C. after the course of 20 min. A yellowish, thick suspension was formed. After 30 min at 25° C., 15.0 g (0.25 mmol) of cyanogen chloride gas were introduced after the course of 25 min. The suspension, which was now more readily stirrable, was transferred to an autoclave and stirred at 60° C. for 17 h. The reaction mixture was poured onto an ice/water mixture (200 ml) and stirred at 0° C. for 30 min. The resulting solid was filtered off and washed with 50 ml of water. After drying in a high vacuum, 20.81 g of crude product were obtained in the form of a beige solid having a concentration of about 68% (GC). This corresponded to a yield of 74.1% of methyl 4-(4-fluorophenyl)-6-isopropyl-2-(N-methanesulphonyl-N-methylamino)pyrimidine-5-carboxylate.

EXAMPLE 19

Methyl 4-(4-fluorophenyl)-6-isopropyl-2-(N-methanesulphonyl-N-methylamino)pyrimidine-5-carboxylate Ib, $R^1=R^2=R^3$=Methyl, $R^4$=Isopropyl, $TiCl_4$, Chlorobenzene 10.0 g (37.7 mmol) of methyl 2-[1-amino-1-(4-fluorophenyl)methylene]-4-methyl-3-oxopentanoate were introduced into 50 ml of chlorobenzene together with 10.17 g (75.4 mmol) of N-cyano-N-methylmethanesulphonamide and the mixture was treated at room temperature with 7.22 g (37.7 mmol) of titanium tetrachloride. The reaction progressed exothermically. The red-orange-coloured suspension was heated to 110–120° C. and stirred for 3.5 h. It was then cooled to room temperature and treated with 30 ml of water. The organic phase was separated off and the aqueous phase was extracted with methylene chloride (30 ml). The combined organic phases were washed with 30 ml of water and dried over magnesium sulphate. After filtering and concentrating the solution in a water-jet vacuum and drying in vacuo, 11.48 g of crude product were obtained in the form of a tacky solid.

Yield: 37.8% [concentration (HPLC) 47.3%].

Example 20

Methyl 4-(4-fluorophenyl)-6-isopropyl-2-(N-methanesulphonyl-N-methylamino)pyrimidine-5-carboxylate Ib, $R^1=R^2=R^3=$Methyl, $R^4=$Isopropyl, $TiCl_4$, Chlorobenzene 10.0 g (37.7 mmol) of methyl 2-[1-amino-1-(4-fluorophenyl)methylene]-4-methyl-3-oxopentanoate were introduced into 50 ml of chlorobenzene together with 10.17 g (75.4 mmol) of N-cyano-N-methylmethanesulphonamide and the mixture was treated at room temperature with 14.45 g (75.4 mmol) of titanium tetrachloride. The reaction progressed exothermically. The red-orange-coloured suspension was heated to 110° C. and stirred for 17.5 h. It was then cooled to room temperature and treated with 30 ml of water. The organic phase was separated off and the aqueous phase was extracted with methylene chloride (2×30 ml). The combined organic phases were washed with 30 ml of water and dried over magnesium sulphate. After filtering and concentrating the solution in a water-jet vacuum and drying in vacuo, 12.92 g of crude product were obtained in the form of a brownish oil.

Yield: 23.3% [concentration (HPLC) 25.9%].

Example 21

Methyl 4-(4-fluorophenyl)-6-isopropyl-2-(N-methanesulphonyl-N-methylamino)pyrimidine-5-carboxylate Ib, $R^1=R^2=R^3=$Methyl, $R^4=$Isopropyl, $TiCl_4$, Toluene 10.0 g (37.7 mmol) of methyl 2-[1-amino-1-(4-fluorophenyl)methylene]-4-methyl-3-oxopentanoate were introduced into 50 ml of toluene together with 10.17 g (75.4 mmol) of N-cyano-N-methylmethanesulphonamide and the mixture was treated at room temperature with 3.61 g (18.9 mmol) of titanium tetrachloride. The reaction progressed exothermically. The red-orange-coloured suspension was heated to 110° C. and stirred for 4.5 h. It was then cooled to room temperature and treated with 30 ml of water. The organic phase was separated off and the aqueous phase was extracted with ethyl acetate (30 ml). The combined organic phases were washed with 30 ml of water and dried over magnesium sulphate. After filtering and concentrating the solution in a water-jet vacuum and drying in vacuo, 11.54 g of crude product were obtained in the form of a tacky oil.

Yield: 13.5% [concentration (HPLC) 16.8%].

Example 22

Methyl 4-(4-fluorophenyl)-6-isopropyl-2-(N-methanesulphonyl-N-methylamino)pyrimidine-5-carboxylate Ib, $R^1=R^2=R^3=$Methyl, $R^4=$Isopropyl, $TiCl_4$, Chlorobenzene 10.0 g (37.7 mmol) of methyl 2-[1-amino-1-(4-fluorophenyl)methylene]-4-methyl-3-oxopentanoate were introduced into 50 ml of chlorobenzene together with 5.08 g (37.7 mmol) of N-cyano-N-methylmethanesulphonamide and the mixture was treated at room temperature with 7.22 g (37.7 mmol) of titanium tetrachloride. The reaction progressed exothermically. The red-orange-coloured suspension was heated to 110–120° C. and stirred for 5 h. It was then cooled to room temperature and treated with 30 ml of water. The organic phase was separated off and the aqueous phase was extracted with methylene chloride (2×30 ml). The combined organic phases were washed with 30 ml of water and dried over magnesium sulphate. After filtering and concentrating the solution in a water-jet vacuum and drying in vacuo, 12.02 g of crude product were obtained in the form of a tacky oil.

Yield: 15.0% [concentration (HPLC) 17.9%].

Example 23

Methyl 3-amino-2-[1-(4-fluorophenyl)methanoyl]-4-methylpent-2-enoate

VI, $R^3=R^4=$Methyl 5.00 g of methyl 4-fluorobenzoylacetate (24.2 mmol, concentration 95%) and 1.69 g of isobutyronitrile (24.2 mmol, concentration 98%) were dissolved in 25 ml of toluene and treated with 7.01 g of tin tetrachloride (26.6 mmol, concentration >99%) at room temperature after the course of 10 minutes. After 3 h at room temperature, the mixture was heated to 80° C. After 11.5 h, the suspension was again cooled to room temperature and treated with 25 ml of water. The mixture was diluted with 10 ml of ethyl acetate and the phases were separated. The organic phase was washed twice with 10 ml of 1N sodium hydroxide solution and concentrated in vacuo (40° C./25 mbar) after drying over magnesium sulphate. 6.18 g of crude product were obtained in the form of a yellow oil. After chromatography on silica gel (eluent: hexane/ethyl acetate 1.5:1), 3.84 g of methyl 3-amino-2-[1-(4-fluorophenyl)methanoyl]-4-methylpent-2-enoate were obtained in the form of an oil.

Yield: 59.0%; concentration (HPLC): 98.6%.

GC-MS: $M^+=265.0$ $^1$H NMR (CDCl$_3$, 400 MHz): δ=0.98 (d); 1.25 (d); 2.90 (sept); 3.34 (s); 3.47 (s); 3.52 (sept); 5.50 (s, broad); 5.90 (s, broad); 7.08 (m); 7.50 (dd); 7.85 (dd); 9.04 (s, broad); 10.86 (s, broad).

$^{13}$C NMR (CDCl$_3$, 100 MHz): δ=20.68 (q); 20.76 (q); 30.58 (d); 30.78 (d); 50.57 (q); 51.17 (q); 96.86 (s); 101.09 (s); 114.85 (d); 115.06 (d); 115.16 (d); 115.37 (d); 128.67 (d); 128.76 (d); 131.33 (d); 131.42 (d); 136.98 (s); 137.01 (s); 139.37 (s); 139.40 (s); 162.48 (s); 164.04 (s); 164.95 (s); 166.56 (s); 169.33 (s); 170.33 (s); 171.58 (s); 175.91 (s); 193.24 (s); 194.40 (s).

Example 24

Methyl 3-amino-2-[1-(4-fluorophenyl)methanoyl]-4-methyl-pent-2-enoate

VI, $R^3=R^4=$Methyl 39.2 g of methyl 4-fluorobenzoylacetate (0.20 mmol) and 16.8 g of isobutyronitrile (0.24 mol, concentration >99%) were dissolved in 200 ml of toluene and treated with 57.9 g of tin tetrachloride (0.22 mmol, concentration >99%) at room temperature after the course of 10 minutes. After 30 min at room temperature, the mixture was heated to 80° C. After 8 h, the suspension was again cooled to room temperature and treated with 200 ml of water. The mixture was diluted with 200 ml of ethyl acetate and the phases were separated. The organic phase was washed twice with 40 ml of 1N sodium hydroxide solution and concentrated in vacuo (40° C./25 mbar) after drying over magnesium sulphate. 50.9 g of crude product were obtained in the form of a yellow oil. After chromatography of 12.0 g of crude product on silica gel (eluent: hexane/isopropanol 90:10), 10.08 g of methyl 3-amino-2-[1-(4-fluoro-phenyl)methanoyl]-4-methylpent-2-enoate were obtained in the form of a yellowish oil.

Yield: 86.3%; (concentration: >99%).

Example 25

Methyl 4-(4-fluorophenyl)-6-isopropyl-2-(N-methanesulphonyl-N-methylamino)pyrimidine-5-carboxylate

Ib, $R^1=R^2=R^3$=Methyl, $R^4$=Isopropyl 2.65 g (10.0 mmol) of methyl 3-amino-2-[1-(4-fluorophenyl)methanoyl]-4-methylpent-2-enoate were introduced into 5.52 g (50.0 mmol) of N-methylmethanesulphonamide and 1.48 g (20.0 mmol) of tert-butanol. 4.95 g (50.0 mmol) of sodium tert-butoxide were added to this solution after the course of 2 min between 23 and 52° C. A yellowish, thick suspension was formed. After 1 h, 2.00 g (32.5 mmol) of cyanogen chloride gas were introduced at 25° C. after the course of 20 min. The suspension, which was now more readily stirrable, was stirred for 18 h at 60° C. The reaction mixture was poured onto water (20 ml). The resulting solid was filtered off and washed with water (2×5 ml). After drying in a high vacuum, 740 mg of crude product were obtained in the form of a beige solid having a concentration of 70.0% (HPLC). This corresponded to a yield of 13.6% of methyl 4-(4-fluorophenyl)-6-isopropyl-2-(N-methanesulphonyl-N-methylamino)pyrimidine-5-carboxylate.

Example 26

Methyl 4-(4-fluorophenyl)-6-isopropyl-2-(N-methanesulphonyl-N-methylamino)pyrimidine-5-carboxylate

Ib, $R^1=R^2=R^3$=Methyl, $R^4$=Isopropyl 2.50 g (9.42 mmol) of methyl 3-amino-2-[1-(4-fluorophenyl)methanoyl]-4-methylpent-2-enoate were introduced into 2.08 g (28.3 mmol) of N-methylmethanesulphonamide and 3.49 g (47.1 mmol) of tert-butanol together with 3.79 g (28.3 mmol) of N-cyano-N-methylmethanesulphonamide. 1.87 g (18.8 mmol) of sodium tert-butoxide were added to this suspension at room temperature after the course of 15 min (exothermic). After 4 h at 76° C., the reaction suspension was poured onto 20 g of ice water. The suspension was stirred in an ice bath, and the precipitate was filtered off and washed with water (2×2.5 ml). After drying in a high vacuum, 1.61 g of methyl 4-(4-fluorophenyl)-6-isopropyl-2-(N-methanesulphonyl-N-methylamino)pyrimidine-5-carboxylate were obtained in the form of a pale beige solid.

Yield: 9.8%; concentration (HPLC): 21.9%.

Example 27

Methyl 4-(4-fluorophenyl)-6-isopropyl-2-(N-methanesulphonyl-N-methylamino)pyrimidine-5-carboxylate

Ib, $R^1=R^2=R^3$=Methyl, $R^4$=Isopropyl, Sodium Tert-butoxide, Compound of the Formula IVb Formed in situ 132.6 g (0.50 mol) of methyl 2-[1-amino-1-(4-fluorophenyl)methylene]-4-methyl-3-oxopentanoate were introduced into 276.2 g (2.50 mol) of N-methylmethanesulphonamide and 74.1 g (1.00 mol) of tert-butanol. 243.7 g (2.50 mol) of sodium tert-butoxide were added to this suspension at 30° C. in portions such that the temperature did not rise above 60° C. A yellowish, thick suspension was formed. After 20 min at 28° C., the mixture was heated to 50° C. and 100.0 g (1.63 mol) of cyanogen chloride gas were introduced after the course of 1 h. The suspension, which was now more readily stirrable, was stirred at 60° C. for 19.5 h. The reaction mixture was poured onto water (750 ml) and stirred at room temperature for 15 min. The resulting solid was filtered off and washed with 2×250 ml of water and 2×200 ml of cold methanol. After drying in a high vacuum, 119.1 g of crude product were obtained in the form of a beige solid having a concentration of 90.1% (HPLC). This corresponded to a yield of 56.3% of methyl 4-(4-fluorophenyl)-6-isopropyl-2-(N-methanesulphonyl-N-methylamino)pyrimidine-5-carboxylate.

Example 28

Methyl 4-(4-fluorophenyl)-6-isopropyl-2-(N-methanesulphonyl-N-methylamino)pyrimidine-5-carboxylate

Ib, $R^1=R^2=R^3$=Methyl, $R^4$=Isopropyl, NaOtBu, MMSA, CMMSA 2.97 g (11.2 mmol) of methyl 2-[1-amino-1-(4-fluorophenyl)methylene]-4-methyl-3-oxopentanoate were introduced into 2.45 g (22.4 mmol) of N-methylmethanesulphonamide (MMSA) and 4.19 g (55.9 mmol) of tert-butanol together with 4.51 g (36.6 mmol) of N-cyano-N-methylmethanesulphonamide (CMMSA). 2.22 g (22.4 mmol) of sodium tert-butoxide were added to this suspension at room temperature in portions. An orange-coloured suspension was obtained. It was heated to 50° C. and stirred at 50° C. for 19.9 h. The suspension was poured onto 20 g of ice water, and the precipitate was filtered off and washed with water (2×5 ml). After drying in a high vacuum, 2.91 g of methyl 4-(4-fluoro-phenyl)-6-isopropyl-2-(N-methanesulphonyl-N-methyl-amino)pyrimidine-5-carboxylate were obtained in the form of a pale beige solid having a concentration of 76.4% (HPLC), which corresponds to a yield of 52.1%.

What is claimed is:

1. A process for the preparation of a compound of the formula:

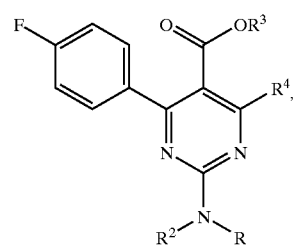

I

In which

R is hydrogen or a group of the formula —$SO_2R^1$;

$R^1$ is $C_{1-6}$-alkyl;

$R^2$ is hydrogen or $C_{1-6}$-alkyl;

$R^3$ is $C_{1-6}$-alkyl; and $R^4$ is $C_{1-6}$-alkyl, comprising in a first stage, reacting a compound of the formula:

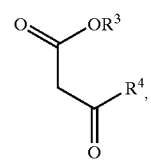

II in which R³ and R⁴ have the above-mentioned meanings, in the presence of a Lewis acid with 4-fluorobenzonitrile to give a compound of the formula:

III in which R³ and R⁴ have the above-mentioned meaning, and, in a second stage, reacting the compound of the formula III with a compound of the formula:

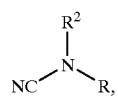

IV in which R and R² have the above-mentioned meanings, to give the final product of the formula I.

2. The process according to claim 1, wherein R and R² are hydrogen, R⁴ is isopropyl and R³ is $C_{1-6}$-alkyl.

3. The process according to claim 2, wherein R³ is methyl.

4. The process according to claim 1, wherein the Lewis acid employed in the first stage is tin tetrachloride.

5. The process according to claim 4, wherein the first stage is carried out in the presence of an organic solvent.

6. The process according to claim 5, wherein the first stage is carried out at a temperature from −5 to 140° C.

7. The process according to claim 6, wherein the second stage is carried out in the presence of an organic solvent, a mixture of water with an organic solvent or in water.

8. The process according to claim 7, wherein the reaction in the second stage is carried out at a temperature from 10 to 120° C.

9. The process according to claim 1, wherein the Lewis acid employed in the first stage is tin tetrachloride.

10. The process according to claim 1, wherein the first stage is carried out in the presence of an organic solvent.

11. The process according to claim 1, wherein the reaction in the first stage is carried out at a temperature from −5 to 140° C.

12. The process according to claim 1, wherein the second stage is carried out in the presence of an organic solvent, a mixture of water with an organic solvent or in water.

13. The process according to claim 1, wherein the reaction in the second stage is carried out at a temperature from 10 to 120° C.

14. The process according to claim 8, wherein the compound of the formula III is isolated by extraction from reaction mixture of the first stage, and then reacted in the reaction of the second stage.

15. The process according to claim 1, wherein the compound of the formula III is isolated by extraction from the reaction mixture of the first stage, and then reacted in the reaction of the second stage.

* * * * *